(12) United States Patent
Hoffmann et al.

(10) Patent No.: US 11,766,386 B2
(45) Date of Patent: Sep. 26, 2023

(54) MEDICAL COMPOSITION CONTAINING GUANIDINYL-CONTAINING POLYMER(S) AND CARRAGEENANE(S)

(71) Applicant: 3M INNOVATIVE PROPERTIES COMPANY, St. Paul, MN (US)

(72) Inventors: Henning Hoffmann, Windach (DE); Peter U. Osswald, Tuerkheim (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 997 days.

(21) Appl. No.: 16/347,306

(22) PCT Filed: Nov. 6, 2017

(86) PCT No.: PCT/US2017/060197
§ 371 (c)(1),
(2) Date: May 3, 2019

(87) PCT Pub. No.: WO2018/128704
PCT Pub. Date: Jul. 12, 2018

(65) Prior Publication Data
US 2019/0282453 A1 Sep. 19, 2019

(30) Foreign Application Priority Data
Nov. 7, 2016 (EP) .................................... 16197469

(51) Int. Cl.
*A61K 6/00* (2020.01)
*A61L 15/60* (2006.01)
(Continued)

(52) U.S. Cl.
CPC ................. *A61K 6/18* (2020.01); *A61K 6/52* (2020.01); *A61K 6/69* (2020.01); *A61K 6/76* (2020.01);
(Continued)

(58) Field of Classification Search
None
See application file for complete search history.

(56) References Cited

U.S. PATENT DOCUMENTS 4,522,593 A 6/1985 Fischer
5,362,495 A 11/1994 Lesage
(Continued)

FOREIGN PATENT DOCUMENTS

DE 202013005258 8/2013
EP 1893163 3/2008
(Continued)

OTHER PUBLICATIONS

Decoteau, Ogledzki, Soroushian, R. D. Perry, Rinse Time of Hemostatic Retraction Pastes, IADR 2011 #1035, https://iadr.abstractarchives.com/abstract/2011sandiego-150036/rinse-time-of-hemostatic-retraction-pastes, 2 pages.
(Continued)

*Primary Examiner* — Dominic Lazaro
(74) *Attorney, Agent, or Firm* — 3M Innovative Properties Company

(57) ABSTRACT

The invention relates to a medical composition comprising guanidinyl-containing polymer(s) and polyanionic polymer(s). The medical composition is useful for absorbing water-containing fluids and can be used as dental retraction composition or as part of a medical treatment device.

18 Claims, 1 Drawing Sheet

(51) Int. Cl.

| | | |
|---|---|---|
| *A61L 15/14* | (2006.01) | |
| *A61L 15/12* | (2006.01) | |
| *A61L 15/18* | (2006.01) | |
| *A61L 15/22* | (2006.01) | |
| *A61K 6/18* | (2020.01) | |
| *A61L 15/28* | (2006.01) | |
| *A61L 15/08* | (2006.01) | |
| *A61K 6/52* | (2020.01) | |
| *A61K 6/69* | (2020.01) | |
| *A61K 6/76* | (2020.01) | |
| *A61C 5/70* | (2017.01) | |
| *C08K 3/36* | (2006.01) | |
| *C08L 5/00* | (2006.01) | |
| *C08L 79/00* | (2006.01) | |

(52) U.S. Cl.
CPC ............ *A61L 15/08* (2013.01); *A61L 15/125* (2013.01); *A61L 15/14* (2013.01); *A61L 15/18* (2013.01); *A61L 15/225* (2013.01); *A61L 15/28* (2013.01); *A61L 15/60* (2013.01); *A61C 5/70* (2017.02); *C08K 3/36* (2013.01); *C08L 5/00* (2013.01); *C08L 79/00* (2013.01); *C08L 2203/02* (2013.01)

(56) References Cited

U.S. PATENT DOCUMENTS

| | | | |
|---|---|---|---|
| 5,712,027 | A | 1/1998 | Ali |
| 5,865,803 | A | 2/1999 | Major |
| 5,893,714 | A | 4/1999 | Arnold |
| 5,927,562 | A | 7/1999 | Hammen |
| 6,383,279 | B1 | 5/2002 | Eckhardt |
| 6,387,354 | B1* | 5/2002 | Bixler .................. A61K 8/73 424/49 |
| 2002/0156149 | A1 | 10/2002 | Schaub |
| 2003/0175217 | A1* | 9/2003 | Kropf .................. A61K 8/02 424/49 |
| 2005/0008583 | A1 | 1/2005 | White |
| 2005/0031850 | A1 | 2/2005 | Mitchell |
| 2005/0250871 | A1 | 11/2005 | Bublewitz |
| 2005/0287494 | A1 | 12/2005 | Yang |
| 2006/0293469 | A1 | 12/2006 | Zech |
| 2007/0004858 | A1 | 1/2007 | Zech |
| 2007/0231291 | A1* | 10/2007 | Huang .................. A61Q 15/00 525/438 |
| 2008/0220050 | A1 | 9/2008 | Chen |
| 2008/0305950 | A1 | 12/2008 | Berrada |
| 2010/0255443 | A1 | 10/2010 | Dragan |
| 2011/0046262 | A1 | 2/2011 | Bublewitz |
| 2011/0151403 | A1 | 6/2011 | Pauser |
| 2012/0077142 | A1 | 3/2012 | Maurer |
| 2012/0295222 | A1 | 11/2012 | Lesage |
| 2014/0186274 | A1* | 7/2014 | Hodgkinson ............ A61K 8/40 424/56 |
| 2014/0348921 | A1 | 11/2014 | Lesage |
| 2016/0115430 | A1 | 4/2016 | Swanson |

FOREIGN PATENT DOCUMENTS

| | | |
|---|---|---|
| JP | 2006-056833 | 3/2006 |
| WO | WO 2006-057535 | 6/2006 |
| WO | WO 2007-128926 | 11/2007 |
| WO | WO 2013-071235 | 5/2013 |
| WO | WO 2015-157261 | 10/2015 |
| WO | WO 2016-164316 | 10/2016 |
| WO | WO 2018-085744 | 5/2018 |

OTHER PUBLICATIONS

Katritzky, "Comprehensive Organic Functional Group Transformation II", Elsevier, 2005, vol. 6, p. 640.
Rose, "Bisdiguanides having antibacterial activity" G. J. Chem Soc., 1956, pp. 4422-4425.
International Search report for PCT International Application No. PCT/US2017/060197 dated Aug. 10, 2018, 5 pages.

* cited by examiner

MEDICAL COMPOSITION CONTAINING GUANIDINYL-CONTAINING POLYMER(S) AND CARRAGEENANE(S)

FIELD OF THE INVENTION

The invention relates to a water-absorbing medical composition containing guanidinyl-containing polymer(s) and carrageenane(s).

The medical composition can be used for various applications, including the use as wound dressing or dental retraction composition.

BACKGROUND ART

For producing of well-fitting dental crowns and bridges, it is typically necessary to first record the current dental situation in the mouth of a patient.

This can be done by using dental impression materials or by scanning the surface of the dental situation in the mouth of the patient, in particular the surface of the prepared tooth or teeth to be reconstructed.

However, besides the necessity to record the immediate visible surface of the dental situation it is also typically necessary to record the so-called preparation margin of the prepared tooth. The preparation margin is typically close to the gumline and may not be easily visible or recordable.

For better access to the preparation margin often a so-called retraction procedure is suggested where a part of the gingiva is temporarily removed from the hard dental structure.

For retracting gingiva from a prepared tooth a cord can be used. In this respect, a retraction cord is packed between gingival tissue and the margin of the prepared tooth (this region is also often called sulcus) using an appropriate dental instrument. To obtain sufficient vertical and horizontal retraction of gingival tissue, it is often necessary to pack several lengths of retraction cord into the sulcus in order to be able to make a detailed dental impression.

A description of the background in regard to retraction cords can be found e.g. in U.S. Pat. No. 4,522,593 (Fischer).

Generally, dental retraction cords are sometimes difficult to place into the gingival sulcus. The procedure can also be time consuming. It can also be cumbersome to remove the retraction cord prior to taking the impression. Coagulated blood may adhere to the cord and removing it may open the wound again which results in bleeding. For a more convenient placement retraction pastes have been suggested.

A commercially available product to be used for retraction is sold under the name Expasyl™. However it has been reported, that Expasyl™ is only effective under specific, limited conditions when the sulcus is flexible and has a sufficient depth. The paste's thickness makes it difficult for some practitioners to express it into the sulcus. Moreover, according to the instruction of use, the viscosity of the composition might change when fluids like water, saliva or blood are absorbed.

Generally, removing non-hardening pastes completely out of the sulcus before taking a dental impression can be very time consuming and cumbersome. Usually, the paste is rinsed off using water-spray. However, sometimes paste residues are located deep in the sulcus and are thus difficult to remove. These residues might prevent the impression material from flowing into the sulcus area and may negatively influence the setting of the impression material which is subsequently applied. Moreover, after rinsing off the paste with water an additional drying step might be required before the impression can be taken. These removing and drying steps could cause bleeding of the tissue and might make an impression taking step more complicated.

Hardening materials are sometimes easier to remove. However, they are not very hydrophilic. This might cause problems with regard to flowability of the material into the gingival sulcus.

Meanwhile a variety of different retraction pastes are known in the dental industry and several pastes are meanwhile available on the market.

A composition for gingival retraction comprising a clay, at least one glass filler, an astringent as well as water is described in US2008/0220050 (Kerr).

U.S. Pat. No. 5,362,495 (Lesage) refers to a method for widening the gingival sulcus without bleeding or oozing, comprising inserting within the gingival sulcus a material in the form of a biocompatible paste which is injectable for external use and having a plastic viscosity measured at 20° C. between about 13,000 and 30,000 Pa*s, wherein said material consisting of a material selected from the group of white clay, seaweed meal and mixtures thereof.

JP 2006/056833 (Yo et al.) relates to a paste consisting of an astringent and filler containing clay mineral, torque, mica, kaolin and/or montmorillonite.

US 2008/0220050 A1 (Chen) relates to a composition for gingival retraction. The pasty composition contains water, clay, glass filler and astringent WO 2006/057535 A1 (Kim) describes a composition comprising a certain amounts of kaolin clay, water, aluminium chloride hexahydrate, starch powder, silicone oil and colouring agent.

US 2005/008583 A1 (White) describes a gingival retraction material comprising a carrying medium, a retraction medium and an anti-evaporating component. As an example the following material formula is given: kaolin powder (80 wt. %), aluminium chloride (15 wt. %), water/glycerine sufficient to produce a heavy plastic consistency, flavourings/colour as desired.

US 2005/0287494 A1 (Yang) describes a gingival retraction material prepared by using fibrillated fibres to improve viscosity and combining taste-modifying agent, colour agent and kaolin filler to form a paste-like structure having the viscosity ranging from $31.0*10^6$ cP to $71.0*10^6$ cP.

US 2012/077142 A1 (Maurer et al.) describes a retraction material containing a mixture of layer type 1:1 silicate filler and a layer type 2:1-silicate mineral filler in a ratio 50/50 to 5/95 wt-% as filler. Additional optional ingredients are water, aluminum chloride as astringent as well as silicone oil. In addition the application describes a capsule as application system for delivering the composition into the sulcus.

A dental retraction material having enhanced fluid absorption is disclosed in US 2010/0255443 (Dragen). Such materials are composed of water, aluminum chloride, sodium polyacrylate as absorbing material and fumed silica.

A composition for gingival retraction comprising a clay, at least one glass filler, an astringent as well as water is described in US2008/0220050 (Kerr).

US 2011/046262 A1 (Bublewitz et al.) discloses a pasty insertion for widening the gingival sulcus containing paste-forming agent, a superabsorber particles and an astringent additive.

US 2014/0348921 A1 (Lesage) describes a retraction paste containing an astringent, preferably aluminum chloride, kaolintic clay, a texturing agent like carrageenane, water (50-70%), and humectant like polyethylene glycol. It is stated that these pastes allow a slower release of aluminium, are less water-sensible and thus allow longer treatment times. But as consequence the rinsability of these pastes is significantly reduced.

US 2010/0255443 A1 (Dragan) describes dental retraction materials which are said to have enhanced fluid absorption. Such materials are composed of water, aluminum chloride, sodium polyacrylate as absorbing material and fumed silica.

DE 20 2013 005258 U1 (Kettenbach) describes dental retraction materials with significant water uptake using water binding fillers like silicates or cotton fibers. However, these materials still do not fully address all needs of a practitioner.

Thus, there is still a need for an improved dental composition, which can be used as a dental retraction material.

DESCRIPTION OF THE INVENTION

According to one aspect, there is a desire for a medical composition having a sufficient capability to absorb fluids, in particular water containing or water based fluids, like blood.

It would also be desirable, if the medical composition can easily be delivered through a thin nozzle.

Ideally, in particular if used for dental retraction purposes, the medical composition should be easily removable if applied into a sulcus of a tooth.

One or more of these objects can be addressed by the medical composition described in the present text.

In one embodiment the invention features a medical composition as described in the present text and the claims comprising guanidinyl-containing polymer(s) and carrageenan(s), in particular carrageenan(s) selected from iota and lambda carrageenan(s). The invention is also related to the use of the medical composition as or for manufacturing a dental retraction material.

If used as dental retraction material, the medical composition typically comprises in addition filler(s) and paste forming liquid(s).

The invention is also related to a kit of parts as described in the present text comprising the medical composition and either of the following components alone or in combination: instruction for use, dental impression material(s), applier(s), and retraction cap(s).

Moreover, described is a method of using the medical composition described in the present text in a process comprising the step of inserting the composition into the sulcus of a tooth.

Another aspect is directed to the use of carrageenane(s) for enhancing the water uptake capability of a medical composition comprising guanidinyl-containing polymer(s).

Another aspect to the invention is directed to a medical treatment device comprising the medical composition described in the present text, wherein the medical treatment device may have the shape of a tape, fixture, wound dressing or bandage.

Unless otherwise specified, within the context of the text of the invention, the following terms have the following meanings.

A "water absorbing composition" is a composition being able to absorb water in an amount of at least 50 wt. % or at least 100 wt. % or at least 200 wt. % with respect to the weight of the composition.

A "medical composition" is a composition for use in the medical field. In this respect the composition should be not detrimental to the patient's health and thus being essentially free of hazardous and toxic components being able to migrate out of the composition.

A "dental composition" is any composition which can be used in the dental or orthodontic field. A dental composition is an embodiment of a medical composition.

A "dental retraction composition" is a composition enabling the practitioner to retract soft dental tissue (e.g. gingiva) away from hard dental tissue (e.g. tooth) before or during an impression of the tooth structure is made.

A "tooth structure" is any tooth structure, prepared or ready for preparation by the dentist. It can be a single tooth or two or more teeth. A tooth structure is also referred to as hard dental tissue in contrast to soft dental tissue (e.g. gingiva).

A "dental impression material" is a material used for making impressions of the tooth structure including the gingiva. A dental impression material is usually applied on a dental impression tray. A dental impression material can be based on different chemical substances and crosslink by various chemical reactions (including addition curing and condensation curing materials). Typical examples include silicone based impression materials (e.g. VPS materials) and polyether based impression materials and mixtures of those.

A "liquid" is any solvent or liquid which is able to at least partially disperse, dissolve or suspend the components being present in the inventive composition at ambient conditions (e.g. 23° C.).

A "paste" is a material that typically consist of a suspension of granular material in a liquid. Pastes can be classified by their viscosity or their consistency comparable to dental impression material (cf. ISO 4823).

A "haemostatic agent" is an agent which is able to reduce bleeding to a certain amount and/or causes blood to coagulate. Haemostatic agents are also sometimes referred to as astringents.

A "particle" means a substance being a solid having a shape which can be geometrically determined. The shape can be regular or irregular. Particles can typically be analysed with respect to e.g. grain size and grain size distribution.

If desired, the particle size can be measured using a Cilas 1064 LD Nass (Cilas, France) light scattering instrument. The Cilas 1064 uses an integrated optical system to cover the range from 0.04 to 500 μm. The mixtures to be analyzed are added to the test chamber filled with water. Ultrasound is applied for about 60 s in order not to alter the particle size distributions and to avoid agglomeration. The raw data is processed with the instrument software using the Fraunhofer approximation, frequently used techniques known to the expert in the art.

"Phyllosilicates" are silicates forming sheets of silicate tetrahedra with $Si_2O_5$. Phyllosilicates can be further divided in sub-groups, e.g. according to the number of sheets or layers arranged with each other.

Within the meaning of the present text, phyllosilicates are divided in the following subgroups: silicate minerals of the 2:1 layer type group and silicate minerals of the 1:1 layer type group.

Clay minerals belong to the group of phyllosilicates can be characterized by the number of layers linked or arranged with each other. This classification is also used in the present text.

E.g., in kaolinite, having the ideal formula $Al_2[Si_2O_5(OH)_4]$), two single layers are linked or arranged with each other.

E.g. in muscovite, having the ideal formula $KAl_2(AlSi_3O_{10})(OH)_2$ and belonging to the mica type group of minerals, three layers are linked or arranged with each other.

The terms "crosslinking", "hardening", "setting", "curing" or "curable" are used interchangeable, all referring to the formation of material with a higher molecular weight and/or to the formation of a material having a higher viscosity, by creating a network due to chemical and/or physical interaction.

A "hardening-", "curing-" or "setting-reaction" is a reaction, wherein physical properties such as viscosity, and tensile strength of a composition change over the time due to a chemical or physical reaction between the individual components.

A composition or solution is "essentially or substantially free of" a certain component, if the composition does not contain said component as an essential feature. Thus, said component is not willfully added to the composition either as such or in combination with other components or ingredient of other components. A composition being essentially free of a certain component usually contains the component in an amount of less than about 1 wt. % or less than about 0.1 wt. % or less than about 0.01 wt. % with respect to the whole composition. Ideally the composition does not contain the said component at all. However, sometimes the presence of a small amount of the said component is not avoidable e.g. due to impurities.

"Ambient conditions" mean the conditions which the inventive solution is usually subjected to during storage and handling. Ambient conditions may, for example, be a pressure of 900 to 1100 mbar, a temperature of 10 to 40° C. and a relative humidity of 10 to 100%. In the laboratory ambient conditions are adjusted to 20 to 25° C. and 1000 to 1025 mbar.

A composition is "essentially or substantially free of" a certain component, if the composition does not contain said component as an essential feature. Thus, said component is not willfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

If not indicated otherwise "molecular weight" always means Mw (weight average of the molecular weight) and can be determined for the individual classes of polymers by gel permeation chromatography (GPC) against a standard of defined molecular weight. Suitable measurement methods are known to the person skilled in the art. If not indicated otherwise, wt. % always refers to the weight of the whole composition.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.). Unless otherwise indicated, all numbers expressing quantities of ingredients, measurement of physical properties such as described below and so forth used in the specification and claims are to be understood as being modified in all instances by the term "about".

The term "comprise" shall include also the terms "consist essentially of" and "consists of".

DETAILED DESCRIPTION

Figure 1A:
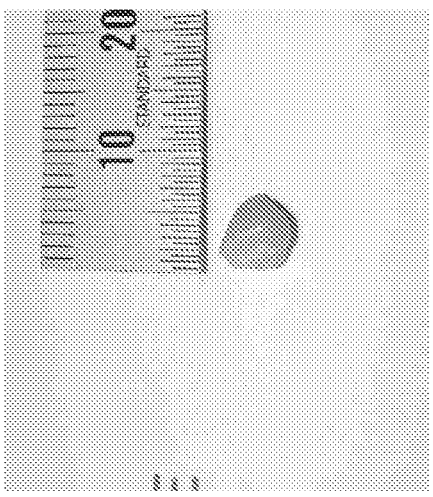
FIG. 1A shows an embodiment of a medical composition as described in the present text before contact with water.

It has been found that the medical composition described in the present text typically shows a couple of advantageous features.

It was found that a medical composition comprising a combination of guanidinyl-containing polymer(s) and carrageenane(s) shows an enhanced capacity of absorbing fluid, like water or water-based fluids.

When the medical composition comes in contact with water based liquids, the composition swells to a multiple of its original volume and forms a soft structure. This structure can be easy removed, even if located in a sulcus of a tooth.

Without wishing to be bound to a certain theory, it seems that there is a synergistic effect if a guanidinyl-containing polymer is used in combination with carrageenane(s).

Further, the use of guanidinyl-containing polymer(s) in the medical composition enables the formulation of a composition with improved storage stability, in particular if the composition is for use as dental retraction composition.

Currently, most dental retraction compositions contain water for dissolving or dispersing other components contained in the composition.

During storage water may evaporate from the composition which typically causes a non-desired increase of the viscosity of the composition.

High viscous compositions typically require a higher force for distributing the composition from a packaging device. In fact, the distribution of a high viscous composition through a thin nozzle into the sulcus of a tooth may become nearly impossible.

To avoid a non-wanted evaporation of water from the composition, the composition has either to be stored under specific conditions (e.g. contained in a sealed blister) or a reduced shelf-life has to be accepted.

It was found that due to the use of guanidinyl-containing polymer(s), the medical composition described in the present text can be formulated essentially without using or adding water.

Thus, the medical composition described in the present text does not contain water in an amount of more than 2 wt. %.

The risk of a non-desired increase of the viscosity due to evaporation of a solvent is thus reduced. Thus, a more storage stable composition can be provided.

Further, the medical composition can be stored in conventional packaging materials without the need for an additional sealed pouch.

In addition, it was found that the flow resistance of the medical composition can be improved, if guanidinyl-containing polymer(s) were used or added.

Moreover, it was found that, if the medical composition is stored in a specific container with a cannula or nozzle having certain dimensions, the composition can be applied to a sulcus using a commercially available dispensing device with acceptable extrusion forces (e.g. less than or equal to about 150 N).

Finally, due to the astringent properties of the guanidinyl-containing polymer(s), the amount of further, more aggressive astringents like aluminium salts (e.g. aluminium chloride) or other heavy metal salts which are typically used for this purpose can be reduced.

Being able to provide a composition containing a reduced amount or being essentially free of aluminium chloride or other heavy metal salts as astringents, can be beneficial as this may contribute to a better compatibility of the medical composition with packaging materials.

If desired, the medical composition described in the present text can be provided as a paste, which can be obtained e.g. by dispersing guanidinyl-containing polymer(s), carrageenan and filler(s) in paste forming liquid(s).

In certain embodiments the medical composition, in particular if provided as a paste, fulfils at least one or more, sometimes all of the following parameters:

If desired, the medical composition can be characterized by one or more of the following features:
 a) pH: from 6 to 10 or 7 to 9, if determined with wet pH sensitive paper;
 b) Water uptake: at least 100% or at least 150% or at least 200%;
 c) Gap Resistance: at least 2.0 mm or at least 2.5 mm or at least 3.0 mm;
 d) Extrusion force: less than or equal to 150 N or below 140 N or below 130 N, e.g. if the medical composition is dispensed from a container having a cannula with the dimension shown in FIG. 4 using a piston as shown in FIGS. 5 and 6 of WO 2010/138433;
 e) Rinsing time: less than or equal to 20 or less than or equal to 15 s.

If desired, the respective features can be determined as described in the example section. In certain embodiments, the combination of the following features is sometimes desirable: b), c) and e).

As there is no need to add astringents like aluminium chloride, the pH value is typically in a range from 6 to 10 or 7 to 9.

The composition typically has a sufficient good storage modulus (e.g. at least about 2,000 kPa).

If the medical composition is used as dental retraction composition and does not have a sufficient storage modulus, it will be difficult to apply into the sulcus.

The tooth surrounding tissue forming the sulcus and having certain elasticity often repels the applied composition. That is, if the storage modulus is too low, the paste will be partly squeezed out of the sulcus which may result in an inefficient retraction. By applying to and/or packing the dental retraction composition e.g. with the aid of a nozzle or cannula, into the sulcus, a sufficient mechanical retraction of the gingiva can be achieved.

According to one embodiment, the medical composition described in the present text comprises paste forming liquid(s).

The nature and structure of paste forming liquid(s) is not particularly limited, either unless the desired result cannot be achieved.

Paste forming liquid(s) include those, which are able to form a paste with the other components present.

Paste forming liquid(s) are typically present, if the medical composition shall be used as dental retraction material.

The paste forming liquid(s) can typically be characterized by one or more of the following features:
 Molecular weight (Mn): utmost 10,000 g/mol;
 Boiling point: above 100° C.;
 Viscosity: up to 35 Pa*s at 23° C.

A molecular weight as outlined above can be beneficial because the risk of an undesired evaporation of the paste forming liquid(s) from the dental retraction composition can be reduced.

A viscosity in the above range can be beneficial because it allows an easy production of a desired paste.

Paste forming liquid(s) which can be used include polar and non-polar liquids and mixtures thereof.

Specific examples include mono-alcohols, glycols (including ethylene glycol, propylene glycol) and the respective alkyl ethers, block-co-polymers of ethylene glycol and propylene glycol (commercially available e.g., as Synperonic® and Pluronic®), copolymers of ethylene glycol, propylene glycol and/or tetrahydrofuran, and alkoxylated glycerine or pentaerythritol or other multifunctional alcohols.

In particular, the following paste forming liquid(s) were found to be useful: polyethylene glycol, polypropylene glycol and mixtures thereof.

The amount of paste forming liquid in the composition is not particularly limited, unless the desired advantages cannot be obtained.

If the amount of paste forming liquid in the composition is too low, the viscosity of the composition typically increases having the result that the extrusion force needed for dispensing the composition from a container might increase as well.

If the amount of paste forming liquid in the composition is too high, the viscosity of the composition typically decreases having the result that the flow resistance might be insufficient and may hamper the application of the composition into the sulcus.

The paste forming liquid(s) are typically present in the following amounts:
 Lower limit: at least 10 or at least 20 or at least 25 wt. %;
 Upper limit: utmost 60 or utmost 55 or utmost 50 wt. %;
 Range: from 10 to 60 or from 20 to 55 or from 25 to 50 wt. %;
 wt. % with respect to the total amount of the dental retraction composition.

According to one embodiment, the medical composition described in the present text comprises filler(s).

Filler(s) in addition to paste forming liquid(s) are typically present, if the medical composition shall be used as dental retraction material.

A wide variety of inorganic, hydrophilic or hydrophobic fillers may be employed such as silicates, silicas (including quartz and cristobalite), aluminas, magnesias, titanias, inorganic salts, metallic oxides and glasses.

Other suitable filler(s) include plastic powder, micro- and nanocrystalline cellulose and starch.

The sizes and surface areas of the filler particles can be adjusted to control the viscosity and thixotropicity of the resulting compositions. Some or all of the fillers may be superficially treated with one or more silanating agents, as known to those of ordinary skill in the art. Such silanating may be accomplished through use of known halogenated silanes or alkoxysilanes or silazanes.

A combination of reinforcing and non-reinforcing fillers can be preferred.

In this respect, the quantity of reinforcing fillers can range from 1 to 10 wt.-%, in particular from 2 to 5 wt.-% with respect to the whole composition. Typical reinforcing fillers include fumed silica, and the like.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Typical non-reinforcing fillers are phyllosilicates, quartz, cristobalite, precipitated silicas, diatomaceous earth, aluminas, magnesias, titanium dioxide, zirconium silicate, metallic oxides, barium sulphate, calcium carbonate, plaster, glass and the like.

The non-reinforcing fillers can be surface treated, e.g. silanated, or non-surface treated.

Typical average particle sizes are from 2 to 10 μm.

If present, the filler(s) are typically present in the following amounts:

Lower limit: at least 3 or at least 5 or at least 10 wt. %;
Upper limit: utmost 70 or utmost 60 or utmost 50 wt. %;
Range: from 3 to 70 or from 5 to 60 or from 10 to 50 wt. %;
wt. % with respect to the total amount of the dental retraction composition.

If a filler is present, the use of phyllosilicates as filler(s) is sometimes preferred. The nature and structure of the phyllosilicate(s) is not particularly limited unless the desired result cannot be achieved.

Phyllosilicates which can be used include layer type 1:1 silicate minerals, layer type 1:2 silicate minerals and mixtures of layer type 1:1 silicate minerals and layer type 1:2 silicate minerals.

Phyllosilicates from the layer type 1:1 silicate mineral which can be used include kaolinite, lizardite, halloysite and mixtures or combinations thereof, wherein kaolinite is sometimes preferred.

The particle size of the layer type 1:1 silicate mineral is not particularly limited, unless the resulting paste gets to inhomogeneous.

The mean particle size is typically in a range between 0.01 and 100 μm or between 0.1 and 50 μm or between 1 and 25 μm.

The content of the layer type 1:1 silicate mineral in the composition is not particularly limited, unless the desired advantages cannot be obtained.

If present, the layer type 1:1 silicate mineral is typically present in an amount from 3 wt. % to 55 wt. % or from 5 wt. % to 50 wt. % with respect to the whole composition.

Phyllosilicates from the layer type 2:1 silicate minerals which can be used include mica minerals, talc-pyrophyllite minerals, smectite minerals, vermiculite minerals, illites minerals.

Specific examples include talc, willemseite, pyrophyllite, stevensite, saponite (from the talc-pyrophyllite type group of minerals), stevensite, sponite, sauconite, hectorite, montmorillonite, beidellite, nontronite, volkonskite (from the smectite type group of minerals), phlogopite, biotite, lepidolite, muscovite, illite, glauconite, celadonite (from the mica type group of minerals).

Layer type 2:1 silicate minerals which do not significantly swell when combined with water or show essentially no swelling at all, were found to be especially beneficial. Those silicate minerals include muscovite and phlogopite. For example, the silicate mineral bentonite was found to be not particularly useful as it shows certain undesirable water solubility.

The particle size of the layer type 2:1 silicate mineral is not particularly limited, unless the resulting composition gets too inhomogeneous.

The mean particle size is typically between 0.01 and 100 μm or between 0.1 and 50 μm or between 1 and 25 μm.

The content of the layer type 2:1 silicate mineral in the composition is not particularly limited, unless the desired advantages cannot be obtained.

If present, the layer type 2:1 silicate mineral is typically present in an amount from 3 wt. % to 55 wt. % or from 5 wt. % to 50 wt. % with respect to the whole composition If a combination of layer type 1:1 silicate minerals and layer type 1:2 silicate minerals is used, the layer type 1:1 silicate mineral and the layer type 2:1 silicate mineral are typically present in the dental retraction composition in a certain weight ratio with respect to each other. This weight ratio includes a range from 50/50 to 5/95 or from 30/70 to 10/90.

That is, the content of the layer type 1:1 silicate mineral and the content of the layer type 2:1 silicate mineral in the dental retraction composition can be about equal.

The layer type 2:1 silicate mineral may also be present in excess compared to the layer type 1:1 silicate mineral.

If a combination of phyllosilicate(s) is desired, the following mixtures can be used:

layer type 1:1 siliates selected from kaolinite, lizardite, halloysite,
layer type 1:2 siliates selected from mica minerals, talc-pyrophyllite minerals,
smectite minerals, vermiculite minerals, illites minerals.

If present, the phyllosilicate(s) are typically present in the following amounts:

Lower limit: at least 3 or at least 5 or at least 8 wt. %;
Upper limit: utmost 60 or utmost 55 or utmost 50 wt. %;
Range: from 3 to 60 or from 5 to 55 or from 8 to 50 wt. %;
wt. % with respect to the total amount of the dental retraction composition.

The medical composition described in the present text comprises a guanidinyl-containing polymer.

It was found that the use of a guanidinyl-containing polymer enables the practitioner the formulation of medical compositions with either a reduced amount or even without the need for an additional astringent such as aluminium chloride and/or the formulation Alternatively, or in addition, the formulation of compositions being essentially free of added water is now possible.

Further, the use of a guanidinyl-containing polymer may help to reduce the extrusion force and/or flow resistance of the medical composition.

The term "guanidinyl-containing polymer" includes also polymers where the guanidinyl moiety is present in its protonated form including the salts thereof (in particular chloride and sulphate salts).

Suitable polymers include polyvinylamine, poly(N-methylvinylamine), polyallylamine, polyallylmethylamine, polydiallylamine, poly(4-aminomethylstyrene), poly(4-aminostyrene), poly(acrylamide-co-methylaminopropylacrylamide), poly(acrylamide-co-aminoethylmethacrylate), polyethylenimine, polypropylenimine, polylysine, polyaminoamides, polydimethylamine-epichlorohydrin-ethylenediamine, polyaminosiloxanes, dendrimers formed from polyamidoamine and polypropylenimine, biopolymers, polyacrylamide homo- or copolymers, amino-containing polyacrylate homo- or copolymers, For some embodiments, the preferred amino-containing polymers include polyaminoamides, polyethyleneimine, polyvinylamine, polyallylamine, polydiallylamine and acrylamide based polymers.

As used herein, the term "guanidinyl" refers to a group of the following formula

If the guanidinyl group is part of a pendant group, the group $R^3$ refers to hydrogen, $C_1$-$C_{12}$ (hetero)alkyl, or $C_5$-$C_{12}$ (hetero)aryl.

If the guanidinyl group is part of the backbone of the polymer, the group $R^3$ can refer to a residue of a polymer chain.

Each group $R^4$ is independently hydrogen, $C_1$-$C_{12}$ (hetero)alkyl, or $C_5$-$C_{12}$ (hetero)aryl. Group $R^5$ is hydrogen, $C_1$-$C_{12}$ (hetero)alkyl, $C_5$-$C_{12}$ (hetero)aryl, or a group of formula —$N(R^4)_2$.

The guanidinyl group can be part of a biguanidinyl group that is of formula —$NR^3$—$C(=NR^4)$—$NR^4$—$C(=NR^4)$—$NR^4R^5$ where the groups $R^3$, $R^4$, and $R^5$ are the same as defined above.

Although any guanidinyl-containing polymer can be used in the cationic form, this polymer is often of Formula (I).

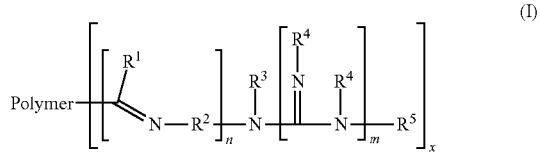

In Formula (I), the group $R^1$ is hydrogen, $C_1$-$C_{12}$ (hetero)alkyl, or $C_5$-$C_{12}$ (hetero)aryl, or a residue of the polymer chain. The group $R^2$ is a covalent bond, a $C_2$-$C_{12}$ (hetero)alkylene, or a $C_5$-$C_{12}$ (hetero)arylene. The group $R^3$ is H, $C_1$-$C_{12}$ (hetero)alkyl, or $C_5$-$C_{12}$ (hetero)aryl, or can be a residue of the polymer chain when n is 0. Each group $R^4$ is independently hydrogen, $C_1$-$C_{12}$ (hetero)alkyl, or $C_5$-$C_{12}$ (hetero)aryl. The group $R^5$ is hydrogen, $C_1$-$C_{12}$ (hetero)alkyl, $C_5$-$C_{12}$ (hetero)aryl, or —$N(R^4)_2$. The variable n is equal to 0 or 1 depending on the precursor polymer used to form the guanidinyl-containing polymer. The variable m is equal to 1 or 2 depending on whether the cationic group is a guanidinyl or biguanidinyl group. The term "Polymer" in Formula (I) refers to all portions of the guanidinyl-containing polymer except the x groups of formula —[$C(R^1)=N$—$R^2$—]$_n$$N(R^3)$—[$C(=NR^4)$—$NR^4R^5$—]$_m$. The term x is a variable equal to at least 1.

Most guanidinyl-containing polymers have more than one guanidinyl group. The number of guanidinyl groups can be varied depending the method used to prepare the guanidinyl-containing polymer. For example, the number of guanidinyl groups can depend on the choice of precursor polymer selected for reacting with a suitable guanylating agent. In some embodiments, the variable x can be up to 1000, up to 500, up to 100, up to 80, up to 60, up to 40, up to 20, or up to 10.

The guanidinyl-containing polymer of Formula (I) is often the reaction product of (a) a precursor polymer and (b) a suitable guanylating agent.

The precursor polymer is often an amino-containing polymer or a carbonyl-containing polymer. When the precursor polymer is an amino-containing polymer, the variable n in Formula (I) is typically equal to 0. When the precursor polymer is a carbonyl-containing polymer, the variable n is equal to 1. If the guanylating agent contains a guanidinyl group or a precursor of a guanidinyl group, the variable m in Formula (I) is equal to 1. If the guanylating agent contains a biguanidinyl group or a precursor of a biguanidinyl group, the variable m in Formula (I) is equal to 2.

In embodiments where n is 0, the base polymer of the guanidinyl-containing polymer is often prepared by reaction of a suitable guanylating agent and an amino-containing polymer. In other embodiments, where n is 1, the guanidinyl-containing polymer is often prepared by reaction of a suitable guanylating agent and a carbonyl-containing polymer.

In those embodiments where n is 0 and the precursor polymer is an amino-containing polymer, the structure of the guanidinyl-containing polymer of Formula (I) can also be written more simply as the structure of Formula (II).

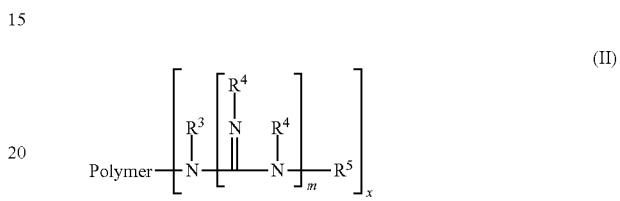

In Formula (II), the group $R^3$ is hydrogen, $C_1$-$C_{12}$ (hetero)alkyl, or $C_5$-$C_{12}$ (hetero)aryl, or can be a residue of the polymer chain. When the guanidinyl group is part of a pendant group, $R^3$ is hydrogen, $C_1$-$C_{12}$ (hetero)alkyl, or $C_5$-$C_{12}$ (hetero)aryl. Each $R^4$ is independently hydrogen, $C_1$-$C_{12}$ (hetero)alkyl, or $C_5$-$C_{12}$ (hetero)aryl. The group $R^5$ is hydrogen, $C_1$-$C_{12}$ (hetero)alkyl, or $C_5$-$C_{12}$ (hetero)aryl, or —$N(R^4)_2$. The variable m is equal to 1 or 2. The term "Polymer" in Formula (II) refers to all portions of the guanidinyl-containing polymer except the x groups of formula —$N(R^3)$—[$C(=NR^4)$—$NR^4R^5$—]$_n$. The term x is a variable equal to at least 1.

The amino-containing polymer used as a precursor polymer to prepare a guanidinyl-containing polymer of Formula (II) can be represented by the formula Polymer —$N(R^3)H$. As noted above, however, the amino-containing polymer typically has many groups —$N(R^3)H$ but Formula (I) shows only one for ease of discussion purposes only. The —$N(R^3)H$ groups can be a primary or secondary amino group and can be part of a pendant group or part of the backbone of the precursor polymer. The amino-containing polymers can be synthesized or can be naturally occurring biopolymers. Suitable amino-containing polymers can be prepared by chain growth or step growth polymerization procedures with amino-containing monomers. These monomers can also, if desired, be copolymerized with other monomers without an amino-containing group. Additionally, the amino-containing polymers can be obtained by grafting primary or secondary amine groups using an appropriate grafting technique.

The guanidinyl-containing polymer also includes polymers where the guanidinyl moiety is protonated including polymers having the following formula:

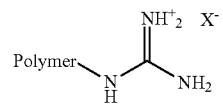

with $X^-$ being selected from $Cl^-$, $Br^-$, $I^-$, $\frac{1}{2}SO_4^{2-}$, $NO_3^-$, $CH_3COO^-$, $C_3H_7COO^-$.

Examples of amino-containing polymers suitable for use, which are prepared by chain growth polymerization include, but are not limited to, polyvinylamine, poly(N-methylvinylamine), polyallylamine, polyallylmethylamine, polydiallylamine, poly(4-aminomethyl styrene), poly(4-aminostyrene), poly(acrylamide-co-methylaminopropylacrylamide), and poly(acrylamide-co-aminoethylmethacrylate).

Examples of amino-containing polymers suitable for use, which are prepared by step growth polymerization include, but are not limited to, polyethylenimine, polypropylenimine, polylysine, polyaminoamides, polydimethylamine-epichlorohydrin-ethylenediamine, and any of a number of polyaminosiloxanes, which can be prepared from monomers such as aminopropyltriethoxysilane, N-(2-aminoethyl)-3-aminopropyltrimethoxysilane, N-trimethoxysilylpropyl-N-methylamine, and bis(trimethoxysilylpropyl)amine.

Other useful amino-containing polymers that have primary or secondary amino end groups include, but are not limited to, dendrimers (hyperbranched polymers) formed from polyamidoamine (PAMAM) and polypropylenimine. Exemplary dendrimeric materials formed from PAMAM are commercially available under the trade designation "STARBURST (PAMAM) dendrimer" (e.g., Generation 0 with 4 primary amino groups, Generation 1 with 8 primary amino groups, Generation 2 with 16 primary amino groups, Generation 3 with 32 primary amino groups, and Generation 4 with 64 primary amino groups) from Aldrich Chemical (Milwaukee, Wis.). Dendrimeric materials formed from polypropylenimine are commercially available under the trade designation "DAB-Am" from Aldrich Chemical. For example, DAB-Am-4 is a generation 1 polypropylenimine tetraamine dendrimer with 4 primary amino groups, DAB-Am-8 is a generation 2 polypropylenimine octaamine dendrimer with 8 primary amino groups, DAB-Am-16 is a generation 3 polypropylenimine hexadecaamine with 16 primary amino groups, DAB-Am-32 is a generation 4 polypropylenimine dotriacontaamine dendrimer with 32 primary amino groups, and DAB-Am-64 is a generation 5 polypropylenimine tetrahexacontaamine dendrimer with 64 primary amino groups.

Examples of suitable amino-containing polymers that are biopolymers include chitosan as well as starch that is grafted with reagents such as methylaminoethylchloride.

Still other examples of amino-containing polymers include polyacrylamide homo- or copolymers and amino-containing polyacrylate homo- or copolymers prepared with a monomer composition containing an amino-containing monomer such as an aminoalkyl(meth)acrylate, (meth)acrylamidoalkylamine, and diallylamine.

For some embodiments, the preferred amino-containing polymers include polyaminoamides, polyethyleneimine, polyvinylamine, polyallylamine, and polydiallylamine.

Suitable commercially available amino-containing polymers include, but are not limited to, polyamidoamines that are available under the trade designations ANQUAMINE (e.g., ANQUAMINE 360, 401, 419, 456, and 701) from Air Products and Chemicals (Allentown, Pa.), polyethylenimine polymers that are available under the trade designation LUPASOL (e.g., LUPASOL FG, PR 8515, Waterfree, P, and PS) from BASF Corporation (Resselaer, N.Y.), polyethylenimine polymers such as those available under the trade designation CORCAT P-600 from EIT Company (Lake Wylie, S.C.), and polyamide resins such as those available from Cognis Corporation (Cincinnati, Ohio) under the traded designation VERSAMID series of resins that are formed by reacting a dimerized unsaturated fatty acid with alkylene polyamines.

Guanidinyl-containing polymers can be prepared by reaction of the amino-containing polymer precursor with a guanylating agent.

Although all the amino groups of the amino-containing polymer can be reacted with the guanylating agent, there are often some unreacted amino groups from the amino-containing polymer precursor remaining in the guanidinyl-containing polymer. Typically, at least 0.1 mole percent, at least 0.5 mole percent, at least 1 mole percent, at least 2 mole percent, at least 10 mole percent, at least 20 mole percent, or at least 50 mole percent of the amino groups in the amino-containing polymer precursor are reacted with the guanylating agent. Up to 100 mole percent, up to 90 mole percent, up to 80 mole percent, or up to 60 mole percent of the amino groups can be reacted with the guanylating agent. For example, the guanylating agent can be used in amounts sufficient to functionalize 0.1 to 100 mole percent, 0.5 to 90 mole percent, 1 to 90 mole percent, 1 to 80 mole percent, 1 to 60 mole percent, 2 to 50 mole percent, 2 to 25 mole percent, or 2 to 10 mole percent of the amino groups in the amino-containing polymer.

Known guanylating agents for reaction with an amino-containing polymer precursor include, but are not limited to, cyanamide; O-alkylisourea salts such as O-methylisourea sulfate, O-methylisourea hydrogen sulfate, O-methylisourea acetate, O-ethylisourea hydrogen sulfate, and O-ethylisourea hydrochloride; chloroformamidine hydrochloride; 1-amidino-1,2,4-triazole hydrochloride; 3,5-dimethylpyrazole-1-carboxamidine nitrate; pyrazole-1-carboxamidine hydrochloride; N-amidinopyrazole-1-carboxamidine hydrochloride; and carbodiimides such as dicyclohexylcarbodiimide, N-ethyl-N'-(3-dimethylaminopropyl)carbodiimide, and diisopropylcarbodiimide. The amino-containing polymer may also be acylated with guanidino-functional carboxylic acids such as guanidinoacetic acid and 4-guanidinobutyric acid in the presence of activating agents such as EDC (N-[3-(dimethylamino)propyl]-3-ethylcarbodiimide hydrochloride), or EEDQ (2-ethoxy-1-ethoxycarbonyl-1,2-dihydroquinoline). Additionally, the guanidinyl-containing polymer may be prepared by alkylation with chloroacetone guanyl hydrazone, as described in U.S. Pat. No. 5,712,027 (Ali et al.).

Guanylating agents for the preparation of biguanide-containing polymers include sodium dicyanamide, dicyanodiamide and substituted cyanoguanidines such as $N^3$-p-chlorophenyl-N1-cyanoguanidine, $N^3$-phenyl-$N^1$-cyanoguanidine, $N^3$-alpha-naphthyl-$N^1$-cyanoguanidine, $N^3$-methyl-$N^1$-cyanoguanidine, $N^3,N^3$-dimethyl-$N^1$-cyanoguanidine, $N^3$-(2-hydroxyethyl)-$N^1$-cyanoguanidine, and $N^3$-butyl-$N^1$-cyanoguanidine. Alkylene- and arylenebiscyanoguanidines may be utilized to prepare biguanide functional polymers by chain extension reactions. The preparation of cyanoguanidines and biscyanoguanidines is described in detail in Rose, F. L. and Swain, G. J. Chem Soc., 1956, pp. 4422-4425. Other useful guanylating reagents are described by Alan R. Katritzky et al., Comprehensive Organic Functional Group Transformation, Vol. 6, p. 640.

The guanidinyl-containing polymer formed by reaction of an amino-containing polymer precursor and a guanylating agent will have pendent or catenary guanidinyl groups of the Formula (III).

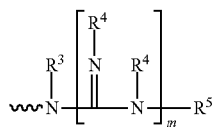 (III)

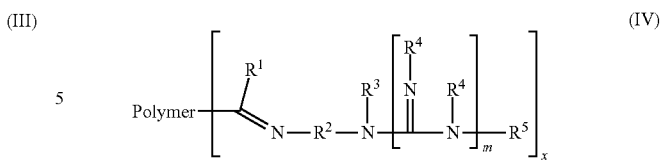 (IV)

In Formula (III), the groups $R^3$, $R^4$, and $R^5$ and the variable m are the same as defined above. The wavy line attached to the $N(R^3)$ group shows the position of attachment the group to the rest of the polymeric material. In most embodiments, the group of Formula (III) is in a pendant group of the guanidinyl-containing polymer.

In some embodiments, it may be advantageous to react the amino-containing polymer precursor to provide other ligands or groups in addition to the guanidinyl-containing group. For example, it may be useful to include a hydrophobic ligand, an ionic ligand, or a hydrogen bonding ligand. This can be particularly advantageous for the removal of certain microorganisms during the wiping of a microorganism-contaminated surface.

The additional ligands can be readily incorporated into the amino-containing polymers by alkylation or acylation procedures well known in the art. For example amino groups of the amino-containing polymer can be reacted using halide, sulfonate, and sulfate displacement reactions or using epoxide ring opening reactions. Useful alkylating agents for these reactions include, for example, dimethylsulfate, butyl bromide, butyl chloride, benzyl bromide, dodecyl bromide, 2-chloroethanol, bromoacetic acid, 2-chloroethyltrimethylammonium chloride, styrene oxide, glycidyl hexadecyl ether, glycidyltrimethylammonium chloride, and glycidyl phenyl ether. Useful acylating agents include, for example, acid chlorides and anhydrides such as benzoyl chloride, acetic anhydride, succinic anhydride, and decanoyl chloride, and isocyanates such as trimethylsilylisocyanate, phenyl isocyanate, butyl isocyanate, and butyl isothiocyanate. In such embodiments 0.1 to 20 mole percent, preferably 2 to 10 mole percent, of the available amino groups of the amino-containing polymer may be alkylated and/or acylated.

The guanidinyl-containing polymer can be crosslinked. The amino-containing polymer can be crosslinked prior to reaction with the guanylating agent. Alternatively, the guanidinyl-containing polymer can be crosslined by reaction of a crosslinker with remaining amino groups from the amino-containing polymer precursor or with some of the guanidinyl groups. Suitable crosslinkers include amine-reactive compounds such as bis- and polyaldehydes such as glutaraldehyde, bis- and polygylcidylethers such as butanedioldiglycidylether and ethyleneglycoldiglycidylether, polycarboxylic acids and their derivatives (e.g., acid chlorides), polyisocyanates, formaldehyde-based crosslinkers such as hydroxymethyl and alkoxymethyl functional crosslinkers, such as those derived from urea or melamine, and amine-reactive silanes, such as 3-glycidoxypropyltrimethoxysilane, 3-glycidoxypropyltriethoxysilane, 5,6-epoxyhexyltriethoxysilane, (p-chloromethyl)phenyltrimethoxysilane, chloromethyltriethoxysilane, 3-isocyanatopropyltriethoxysilane, and 3-thiocyanatopropyltriethoxysilane.

In other embodiments, the guanidinyl-containing polymer is of Formula (IV), which corresponds to Formula (I) where n is equal to 1.

In Formula (IV), the group $R^1$ is hydrogen, $C_1$-$C_{12}$ (hetero)alkyl, or $C_5$-$C_{12}$ (hetero)aryl, or a residue of the polymer chain. If the guanidinyl-containing group is the reaction product of a guanylating agent and a carbonyl group that is part of the backbone of the polymer, $R^1$ is a residue of the polymer chain. Group $R^2$ is a covalent bond, a $C_2$-$C_{12}$ (hetero)alkylene, or a $C_5$-$C_{12}$ (hetero)arylene. Group $R^3$ is hydrogen, $C_1$-$C_{12}$ (hetero)alkyl, or $C_5$-$C_{12}$ (hetero)aryl. Each $R^4$ is independently H, $C_1$-$C_{12}$ (hetero)alkyl, or $C_5$-$C_{12}$ (hetero)aryl. Group $R^5$ is hydrogen, $C_1$-$C_{12}$ (hetero)alkyl, or $C_5$-$C_{12}$ (hetero)aryl, or —$N(R^4)_2$. The variable m is equal to 1 or 2. The term "Polymer" in Formula (I) refers to all portions of the guanidinyl-containing polymer except the x groups of formula —$C(R^1)$=N—$R^2$—$N(R^3)$—[C(=$NR^4$)—$NR^4R^5$—]$_m$ The term x is a variable equal to at least 1.

Guanidinyl-containing polymers of Formula (IV) are the reaction product of a carbonyl-containing polymer and a suitable guanylating agent for reaction with a carbonyl group. The carbonyl-containing polymer used as a precursor polymer to prepare a guanidinyl-containing polymer of Formula (IV) can be represented by the formula Polymer —C(O)—$R^1$. The carbonyl-containing polymer precursor typically has many groups —C(O)—$R^1$ but Formula (IV) shows only one for ease of discussion purposes only. The carbonyl group —C(O)—$R^1$ is an aldehyde group (when $R^1$ is hydrogen) or a ketone groups (when $R^1$ is a (hetero)alkyl or (hetero)aryl). Although the carbonyl-group can be part of the polymeric backbone or part of a pendant group from the polymeric backbone, it is typically in a pendant group.

If desired, the guanidinyl-containing polymers can be produced as described in US 2016/0115430 A1 (Swanson et al.), in particular in sections [0049] to [0080], the description of which is herewith incorporated by reference.

The guanidinyl-containing polymer is typically present in the following amounts:
Lower limit: at least 1 or at least 2 or at least 5 wt. %;
Upper limit: utmost 60 or utmost 40 or utmost 30 wt. %;
Range: from 1 to 60 or from 2 to 40 or from 5 to 30 wt. %;
wt. % with respect to the total amount of the dental retraction composition.

The medical composition described in the present text comprises carrageenane(s).

Carrageenans or carrageenins are a family of sulphated polysaccharides that are typically extracted from red edible seaweeds.

There are three main varieties of carrageenan, which differ in their degree of sulphation.

Kappa-carrageenan has one sulphate group per disaccharide. Iota-carrageenan has two sulphates per disaccharide. Lambda carrageenan has three sulphates per disaccharide. Other carrageenan(s) which are known are epsilon and With respect to the present text, the use of iota or lambda carrageenan(s) can sometimes be preferred.

Carrageenans are large, highly flexible molecules that curl forming helical structures. This gives them the ability to form a variety of different gels at room temperature.

Carrageenans are polysaccharides made up of repeating galactose units and 3,6 anhydrogalactose (3,6-AG), both sulfated and non-sulfated. The units are typically joined by alternating α-1,3 and β-1,4 glycosidic linkages.

If desired, the carrageenane(s) can be characterized by one or more of the following features:
- molecular weight (Mw; weight average): from 10,000 to 1,000,000 or from 20,000 to 500,000 g/mol;
- ester sulphate content: from 25 to 40 wt. % or from 25 to 30 wt. % with respect to the weight of the carrageenan.

The carrageenane(s) is typically present in the following amounts:
- Lower limit: at least 1 or at least 2 or at least 5 wt. %;
- Upper limit: utmost 40 or utmost 35 or utmost 30 wt. %;
- Range: from 1 to 40 or from 2 to 35 or from 5 to 30 wt. %;

wt. % with respect to the total amount of the dental retraction composition.

The ratio of guanidinyl-containing polymer(s) to carrageenan(s) is typically from 4 to 1 to 1 to 4 with respect to weight.

Surprisingly it was found that by using a combination of guanidinyl-containing polymer(s) and carrageenan(s), the water-absorbing properties of the guanidinyl-containing polymer(s) can significantly be increased.

The medical composition described in the present text may further comprise one or more additive(s).

Additives, which can be present in the composition, include colourant(s), pharmaceutical drug(s), anti-microbial agent(s), flavouring agent(s), preserving agent(s), surfactant(s), pH buffering agent(s), antioxidant(s) and mixtures and combinations thereof.

There is no need for additives to be present, however, if one or more additives are present, they are typically present in an amount which supports the intended purpose.

According to one embodiment, the medical composition has a colour which may allow an easy detection (especially in a patient's mouth compared to oral tissue and/or tooth substance) and control whether after the treatment all residues have been removed, in particular if the medical composition is used as dental retraction composition.

E.g., a blue, green or yellow colour may be suitable. However, in view of some new impression techniques like e.g. digital scanning, other colours might be preferred, in particular if the medical composition is used as dental retraction composition. Some techniques prefer colours that are less visible for the scanning instrument e.g. red or white. Colouring of the retraction device can be achieved by incorporating colorants or pigments (organic and inorganic) into the composition.

Examples of colourants which can be used include chinoline yellow dye (sicovit), chromophtalblue A3R, red iron oxide 3395, Bayferrox 920 Z Yellow, Neazopon Blue 807 (copper phthalocyanine-based dye), Helio Fast Yellow ER, Brilliant Blue FCF, Fast Green FCF and/or Orange Yellow S. Pigments or dyes which are stable under acidic conditions are preferred. According to a further embodiment, pharmaceutical drugs can be added.

According to a further embodiment, rheology modifers can be added. Rheology modifiers might contribute to the viscosity and effect the rinsability. Rheology modifiers which can be added include silicone oil.

Pharmaceutical drugs might contribute or enhance a haemostatic effect, e.g. caused by the addition of an astringent. Pharmaceutical drugs which can be added include adrenaline, epinephrine, propylhexidrin, adrenochrom-monosemicarbazone, propylgallat, tranexamic acid, etamsylate, batroxobin, thrombin, fibrin, norepinephrine, noradrenalin, teryzolin, oxymetazolin and other beta-2 Sympathomimetika, In another embodiment of the invention, the dental retraction composition may comprise one or more surfactants.

Typical surfactants, which can be used, include anionic, cationic or non-ionic surfactants.

There is no need for a surfactant to be present at all. However, if a surfactant is present, it is typically present in an amount of up to 2 wt. % or up to 1 wt. % or up to 0.05 wt. %, with respect to the whole composition.

In another embodiment of the invention, the dental retraction composition may comprise a pH buffering agent.

The addition of a pH buffering agent might facilitate adjusting the pH value, in particular making the retraction composition less acidic. Typical pH buffering agents, which can be used, include but are not limited to carbonates and phosphates (e.g. alkali carbonate or alkali bicarbonate).

There is no need for a pH buffering agent to be present at all. However, if a pH buffering agent is present, it is typically present in an amount of up to 10 wt. % or up to 2 wt. % of up to 0.5 wt. %, with respect to the whole composition.

In another embodiment of the invention, the dental retraction composition may comprise a flavouring agent(s) to improve the taste and/or smell of the composition.

Typical flavouring agent(s), which can be used, include but are not limited to Isoamylacetate (banana), Benzaldehyde (bitter almond). Cinnamic aldehyde (Cinnamon), Ethylpropionate (fruity), Methyl anthranilate (Grape), mints (e.g. peppermints), Limonene (e.g. Orange), Allylhexanoate (pineapple), Ethylmaltol (candy), Ethylvanillin (Vanilla), Methylsalicylate (Wintergreen).

There is no need for a flavouring agent to be present at all. However, if a flavouring agent is present, it is typically present in an amount of up to 3 wt. % or up to 0.1 wt. % of up to 0.01 wt. %, with respect to the whole composition.

If present, the additive(s) are typically present in the following amounts:
- Lower limit: at least 0.01 or at least 0.1 or at least 0.5 wt. %;
- Upper limit: utmost 20 or utmost 15 or utmost 10 wt. %;
- Range: from 0.01 to 20 or from 0.1 to 15 or from 0.5 to 10 wt. %;

wt. % with respect to the total amount of the dental retraction composition.

A process of manufacturing the medical composition described in the present text typically comprises the steps of providing the individual components to be mixed and mixing the components.

The medical composition as described in the present text is typically contained in a container.

The medical composition is preferably provided to the practitioner under hygienic conditions. One possibility to achieve this includes packing or storing the medical composition in a sealed container such as a capsule, cartridge or foil bag under hygienic conditions.

A suitable container typically has a front end and a rear end, a piston movable in the container and a nozzle or cannula for delivering or dispensing the composition located in the container. The container has usually only one compartment or reservoir.

A suitable container may have a volume in the range from 0.1 to 1 ml. This is the volume typically needed for a single dental retraction procedure. Such a container is typically used only once (e.g. disposable packing).

If the medical composition is provided as a paste, the medical composition can be dispensed out of the container by moving the piston in the direction of the nozzle. The piston can be moved either manually or with the aid of an application device or applier designed to receive the container (e.g. an application device having the design of a caulk gun).

Examples of containers which can be used include compules, syringes and screw tubes. Containers of this kind are exemplified in more detail e.g. in U.S. Pat. No. 5,927,562 (Hammen et al), U.S. Pat. No. 5,893,714 (Arnold et al.) or U.S. Pat. No. 5,865,803 (Major).

It can be advantageous, if a container is used comprising a nozzle having a shape and size, which allows an easy and safe application of the dental retraction composition in the sulcus.

Useful containers typically have a hollow body (typically of cylindrical or conical shape) with a front end and a rear end in which the dental retraction composition is stored. The rear end is typically sealed with a piston, being movable in the hollow body. At the front end of the hollow body, there is typically a nozzle having a size and shape which enables the practitioner to dispense the medical composition into the sulcus of a patient. The smaller the diameter of the nozzle is, the easier the nozzle can be placed into the sulcus. However, a small diameter of the nozzle may result in an increase of the extrusion force needed to dispense the medical composition out of the device. Thus, not all cannula sizes and diameters are suitable. A device with a nozzle or cannula having an external diameter in the range from 0.6 mm to 1.3 mm and an internal diameter in the range from 0.2 mm to 0.9 mm has been found to be particular useful.

However, other shapes and diameters can be used as well, if the intended effect (i.e. widening of the sulcus) can be achieved.

It has been found that especially a certain container containing the medical composition is particularly suited to address the object of the present invention. Such a container is described in more detail in US 2011/151403 A (Pauser et al.).

If this particular combination is used, the medical composition if used as dental retraction composition can be easily dispensed into the sulcus of a tooth and the desired retraction achieved.

The container which can advantageously be used for storing and dispensing the medical composition comprises a cannula that has a free end which comprises an opening for dispensing the composition.

Such a container facilitates the application of the medical composition into the sulcus of a tooth in that it provides a mechanical means which allows an easy widening of the sulcus with the aid of the cannula. Once the sulcus has been widened, the medical composition can easily be applied and due to its sufficient storage modulus may help stabilizing the widened sulcus.

In one embodiment the free end and the opening are shaped so that the opening can be positioned to the entry of the gingival sulcus, with an outer lateral surface of the free end touching the tooth and the gingiva. The free end is further preferably shaped so that the gingiva is laterally displaced, for example predominantly laterally displaced, from the tooth as the cannula is further moved with the opening toward the inside of the gingival sulcus. Thus, the cannula preferably allows for injecting the medical composition in a pre-opened gingival sulcus which may help to reliably fill the gingival sulcus with the medical composition.

In another embodiment the free end has an outer lateral surface which extends between a first outer diameter D1 and a second outer diameter D2. Preferably the first outer diameter D1 is located adjacent the front of the free end, or at the front most end. The second outer diameter D2 is preferably located at a distance L2 further to the rear from the first outer diameter D1. D2 is preferably greater than D1. This preferably enables the device to displace the gingiva laterally away from the tooth, and preferably thereby enables the device to widen the gingival sulcus as the free end is moved farther into the gingival sulcus.

The term "diameter" may be generally interpreted as "cross-sectional dimension", for cases in which a non-circular cross-section is provided.

The diameter D1 may be between 0.2 mm and 1 mm, in particular between 0.3 mm and 0.7 mm, or between 0.3 mm and 0.8 mm, in more particular D1 may be within a range of 0.4 mm to 0.6 mm. The diameter D1 is preferably about 0.4 mm. A relatively small dimension of the outer diameter D1 preferably allows, for example, the front of the free end to be inserted in the entry of the gingival sulcus relatively easily. Further such dimensions may help to reduce the risk of injuries of the gingival tissue during insertion of the front of the free end in the entry of the gingival sulcus, because it fits between the tooth and the gingiva rather than pressing on the gingiva itself.

The diameter D2 may be between 0.7 mm and 1.4 mm, in particular between 0.7 mm and 1.3 mm, in more particular the diameter D2 may be between 0.9 and 1.3 mm. Preferably the diameter D2 is about 1.1 mm. Such dimensions may for example provide the free end of the cannula with a sufficient stiffness, and on the other hand may still provide good interproximal access for the free end. Therefore, the device described in the present text may be suitable to inject a dental retraction composition in the gingival sulcus all around a tooth in a controlled manner, and not only at distal or lingual portions of the gingival sulcus.

The length L2 of the free end may be between 0.3 mm and 2 mm, in particular between 0.3 mm and 1 mm, and preferably about 0.5 mm.

In another embodiment the first outer diameter D1 is located adjacent the opening. The first outer diameter D1 may also be formed by the opening. The opening may have a first inner diameter P1 which is between 0.2 mm and 1 mm, however the opening may further have a first inner diameter P1 which is between 0.3 mm and 0.7 mm. In particular P1 may be within a range of 0.4 mm to 0.6 mm, and preferably about 0.4 mm. P1 may be smaller than D1, but is preferably about equal to D1. In latter case P1 and D1 both refer to the diameter of the opening. In particular, the inner diameter P1 may provide for the flow rate of a high viscosity dental composition to be controlled relatively precisely as the composition is injected into the gingival sulcus.

In another embodiment the lateral outer surface of the free end tapers from the second outer diameter D2 toward the first outer diameter D1. Thus, the taper preferably tapers in a direction from D2 toward D1. Furthermore the taper preferably tapers based on a curve having a relatively constant radius R. The Radius R may be greater than ½ of D2. For example, the shape of the free end may resemble a nose cone, a convex cone, or a radial cone. A curve resembling a radius greater than ½ of D2 may provide for a relatively low force required to insert the free end of the cannula in the entry of the gingival sulcus. Relative to a linear cone such convex or radial cone may further provide for a less blunt front-most end, which may reduce the risk of injuring the gingiva when inserted into the gingival sulcus.

The cannula of the container may have a length L1 between the first outer diameter D1 and a third outer diameter D3. The cannula may have a shaft portion extending between the second outer diameter D2 and the third outer diameter D3. The shaft portion and the free end may be located adjacent to each other, and together extend along the length L1. The third outer diameter D3 may be between 0.7 mm and 2 mm, in particular between 1.3 mm to 1.9 mm, and preferably about 1.7 mm. D3 is preferably greater than D2, but may also be about equal to D2. Thus, the shaft portion may be generally cylindrical or conical. Preferably the shaft portion smoothly transitions to the free end. The length L1 may be between 6 mm and 18 mm, in particular between 8 mm and 10 mm, and preferably about 9 mm. Such dimensions preferably allow the cannula to access areas that are accessible only through narrow spaces in a patient's mouth, for example a gingival sulcus between two teeth. This may also help in injecting a dental composition around substantially the entire perimeter of a tooth.

In one embodiment the cannula has a marking. The marking preferably is usable as reference with regard to a certain (for example a preferred) penetration depth of the cannula in the gingival sulcus. The marking may help a user to observe and/or to assess the depth to which the cannula is inserted in the gingival sulcus during a treatment of a patient.

Therefore, a user may control the penetration depth of the cannula relatively precisely and thereby may achieve an effective gingival retraction. On the other hand this may help to avoid damage to the gingival tissue which may result from too deep penetration of the cannula in the gingival sulcus. The marking may be a notch, a rim, a step, or a (printed) line, for example. The marking may extend partly or entirely circumferentially around the cannula. The marking may further be formed by a transition between colors of outside surfaces of the cannula. For example, the front end of the cannula may have a certain first outside color, and an adjacent rear portion of the cannula may have a certain second outside color, wherein the first and second colors are different. The marking may also be formed by a transition between areas of different transparency or translucency. Preferably the marking is formed by a transition between surface structures of outside surfaces of the cannula. For example, the front end of the cannula may have a generally even or glossy outside surface, and an adjacent rear portion of the cannula may have a more rough or matt outside surface. The marking may also be a scale marking different penetration depths.

In one embodiment the container comprises a cartridge having a chamber for receiving and storing the dental retraction composition. The container is preferably adapted for comprising a piston, or may comprise a piston. The container is preferably adapted for dispensing the dental retraction composition through the cannula. The cartridge may extend along a longitudinal axis, and the piston may be movable along the longitudinal axis for urging the dental retraction composition towards the cannula. The chamber may, for example open into a nozzle to which the cannula can be adapted. Alternatively the chamber may open into the cannula. The cannula may be fixedly attached to the cartridge. For example, the cannula and the cartridge may be co-injection molded. In another embodiment the cannula and the cartridge are made from different plastic materials. For example the cartridge may be made of a more rigid plastic material than the cannula. Therefore, the cartridge may provide sufficient stability for extruding the composition, and the cannula may be sufficiently soft to reduce the risk of injuries of the gingiva while in use.

In another embodiment the cannula may extend along a longitudinal axis which is inclined relative to the longitudinal axis of the cartridge by an angle of between 30 degrees and 60 degrees, preferably by about 45 degrees. The cannula may also extend along a curve, and a central axis through the opening of the cannula may be inclined relative to the longitudinal axis of the cartridge by an angle of between 30 degrees and 60 degrees, preferably by about 45 degrees.

In another embodiment the cannula comprises a passageway between the opening with the first inner diameter P1 and an inlet with a second inner diameter P2, wherein P2 is between 0.3 and 1.0 mm. P2 is preferably greater than or equal to P1. Thus the passageway may taper towards the opening which may in dispensing certain dental compositions provide for a reduced extrusion force. Alternatively the passageway may be generally cylindrical which may facilitate manufacturing.

In another embodiment the convexly tapered outer surface of the free end may meet with the inner surface of the passageway at an angle of less than 90 degrees. It has been found that an angle below 90 degrees between the outer surface of the free end and the inner surface of the passageway may provide for a relatively low force required to insert the front of the free end into the entry of the gingival sulcus.

Materials which can be used for producing the cannula include polyethylene, polypropylene, styrene-butadiene-styrene block copolymer, styrene-butadiene-methacrylate block copolymer, and thermoplastic polyurethane. Preferred plastic material for the container include polyamide, polyoxymethylene, polypropylene and polycarbonate.

Described is also a kit of parts comprising part A and part B, part A comprising the medical composition as described in the present text and part B comprising one or more of the following components: applier, dental impression material, retraction caps and/or instruction for use.

Thus, the kit of parts may comprise besides a medical composition as described in the present text a dental impression material.

The dental impression materials which can be used in combination with the medical composition are not particularly limited in regard to their chemistry and nature. Polyether moieties or silicone moieties containing impression materials have found to be useful.

Examples of polyether moieties containing impression materials are given in U.S. Pat. No. 6,383,279, US 2002/0156149 and US 2005/02503871. Commercially available materials are sold e.g. under the brand Impregum™.

Examples of silicone moieties containing impression materials are given in EP 1893163, US 2007/004858 and US 2006/293469. Commercially available materials are sold e.g. under the brand Imprint™ (3M ESPE). The kit may also comprise retraction caps.

Retraction caps can be useful for keeping the medical composition if used as dental retraction composition in place until an impression is taken or pushing the dental retraction composition into the sulcus. Retraction caps can be made of soft, tissue friendly material, e.g. cotton. However, other materials might be useful as well. If appropriate a temporary restoration can be used as retraction cap, too. Commercially available retraction caps are e.g. sold under the brand Comprecap™ (Coltene Whaledent).

In some cases compression caps or bridges, temporary crowns or bridges or even a first impression might be used as a kind of accessory during the retraction process. Typically, the dental retraction composition remains in the sulcus for a couple of minutes (e.g. 1 to 10 or 2 to 6 min to achieve effective mechanical retraction. The kit may also comprise an applier or capsule dispenser.

Those devices are commercially available e.g. from 3M Oral Care, 3M ESPE (cf. Product Catalogue 2007, page 29). Typical appliers have a gear ratio from about 3:1 to about 4:1. A further example of an applier, which can be used, is shown in U.S. Pat. No. 5,362,495 (Lesage), FIG. 3.

Described is also a process of dispensing the medical composition as described in the present text, in particular if the medical composition is provided as a paste.

The process typically comprises the following steps:
providing a device or container containing the medical composition as described in the text of the invention,
placing the device or container in an applier or dispenser,
using the applier or dispenser to dispense the medical composition.

These steps can be repeated, if desired.

A method of retracting soft tissue from hard dental tissue typically comprises the steps of
dispensing the medical composition as described in the present text into the sulcus between soft and hard dental tissue,
leaving or retaining the medical composition in the sulcus for at least about 10 s or at least about 30 s or at least about 60 s,
removing the medical composition from the sulcus and optionally making an impression of the hard dental tissue.

Described is also the use of a medical composition as described in the present text for producing a means for retracting soft tissue form hard dental tissue, the means typically comprising a container with a cannula and a reservoir, wherein the composition is stored in the reservoir before use.

According to one embodiment, the medical composition is inserted into the sulcus by the aid of the front end of the cannula of the container. This may facilitate the mechanically opening of the sulcus between soft and hard dental tissue. A typical application procedure can be exemplified as follows:

If used as dental retraction material, the medical composition is dispensed by means of an applier out of a nozzle or cannula of a container into the sulcus of a prepared tooth structure of a mammal or human being. The medical composition remains in the sulcus for an appropriate time period, which is typically determined by the practitioner.

After sufficient retraction, the medical composition is removed from the sulcus using e.g. a dental water air syringe having sufficient pressure. Water-air beam devices are typically included in a dental chair.

The sulcus has been widened due to the application of the medical composition compared to the sulcus before the application. After removal of the medical composition the shape of the prepared tooth including the preparation margin can be determined, either by an impression-taking process with a common impression material or an by an intra-oral scan of the prepared region using e.g. an inter-oral scanner such as the COS System (chair-side oral scanner) provided by 3M Oral Care, 3M ESPE.

If desired the whole process and workability can also be demonstrated in vitro, e.g. using a Frasaco™ Standard Model AG3 (synthetic tissue surrounding an artificial tooth).

According to another embodiment, the medical composition is part of or used as medical treatment device.

The medical treatment device may have the shape of a tape, fixture, wound dressing, bandage or combination thereof.

In use the medical treatment device is placed on a wound to be treated and helps to absorb fluids like blood during the treatment.

Further, due to the swelling properties of the medical composition, the medical composition—if located on a tape and fixed to the wound—may exert additional pressure and contribute to the healing of the wound, e.g. by stopping bleeding.

Further embodiments are described below:

Embodiment 1 relates to a medical composition as described in the present text, in particular for use as dental retraction material, comprising
filler(s): from 3 to 60 wt. %,
paste forming liquid(s): from 10 to 60 wt. %,
guanidinyl-containing polymer(s): from 1 to 60 wt. %;
carrageenane(s): from 1 to 40 wt. %,
wt. % with respect to the weight of the whole composition.

Embodiment 2 relates to a medical composition as described in the present text, in particular for use as dental retraction material, comprising
filler(s) being present in an amount from 3 to 60 wt. %,
paste forming liquid(s) selected from glycol, glycerine, ethylene glycol, poly(ethylene glycol), propylene glycol, poly(propylene glycol), ethylene/propylene glycol co-polymers and mixtures thereof and being present in an amount from 10 to 50 wt. %,
guanidinyl-containing polymer(s): the polymer being a polyethylene imine and being present in an amount from 5 to 30 wt. %,
carrageenane(s) being present from 5 to 30 wt. %,
wt. % with respect to the weight of the whole composition.

Embodiment 3 relates to a medical composition as described in the present text, in particular for use as dental retraction material, comprising
phyllosilicate(s) selected from kaolinite, mica minerals and mixtures thereof and being present in an amount from 10 to 50 wt. %,
paste forming liquid(s) selected from glycol, glycerine, ethylene glycol, poly(ethylene glycol), propylene glycol, poly(propylene glycol), and mixtures thereof and being present in an amount from 10 to 50 wt. %,
guanidinyl-containing polymer(s): the polymer being a polyethylene imine and being present in an amount from 5 to 30 wt. %,
carrageenane(s) being present in an amount from 5 to 30 wt. %.

Embodiment 4 relates to a medical composition as described in the present text, in particular for use as dental retraction material, comprising
phyllosilicate(s) selected from kaolinite, mica minerals and mixtures thereof and being present in an amount from 10 to 50 wt. %,
paste forming liquid(s) selected from glycol, glycerine, ethylene glycol, poly(ethylene glycol), propylene glycol, poly(propylene glycol), silicone oil and mixtures thereof and being present in an amount from 10 to 50 wt. %,
guanidinyl-containing polymer(s): the polymer being a polyethylene imine and being present in an amount from 5 to 30 wt. %,
carrageenane(s) being present in an amount from 5 to 30 wt. %, the medical composition not comprising alone or in combination either of the following:

aluminium salt(s) such as aluminium chloride in an amount above 2 wt. %, water in an amount above 2 wt. %, wt. % with respect to the weight of the whole composition.

The medical composition described in the present text does typically not contain components producing a toxic, injurious, or immunological response in living tissue or components or additives which jeopardize the intended purpose to be achieved with the present invention.

Thus, for examples components or additives added in an amount which finally result in a composition, the characteristics of which are in contradiction to the intended purpose of the invention, are usually not contained in the dental retraction composition.

According to a specific embodiment, the medical composition does typically not contain one or more of the following components:

fibrillated fibres in an amount of more than 2 wt. %;
starch or cellulose in an amount of more than 2 wt. %;
water in an amount of more than 2 wt. %;
cross-linkable component(s) in an amount of more than 2 wt. %;
aluminium chloride in an amount of more than 5 or 2 wt. %.

Fibrillated fibres are e.g. natural fibres based on cellulose or man-made fibres e.g. polyester, polyamide or fibres of glass.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate the invention.

Examples

Unless otherwise indicated, all parts and percentages are on a weight basis, all water is de-ionized water, and all molecular weights are weight average molecular weight.

Moreover, unless otherwise indicated all experiments were conducted at ambient conditions (23° C.; 1013 mbar).

Methods

Rinse Time

If desired, the rinse time can be measured as follows: The pastes are inserted into a 9 mm×1 mm×3 mm crevice in a plastic cone shaped block simulating a gingival sulcus, rinsed therefrom and the time required to clear it was measured. The floor of the crevice is positioned at a 45 degree angle to the line of the water stream. A dental air and water syringe deliveres pressurized air at 2 bars and water at 1.8 bars simultaneously. The tip of the syringe is situated 5 mm from the crevice. The round plastic block underwent 60 rotations per minute.

The measurement of the rinse time is also as described in C. Decoteau, M. Ogledzki, S. Soroushian, R. D. Perry, Rinse Time of Hemostatic Retraction Pastes, IADR 2011 #1025.

Flow Resistance

If desired, the flow resistance can be measured using a testing device Zwick Z020 machine (Zwick Roell Comp.). The testing device is equipped with a mould (diameter 8 mm, depth 5.6 mm) and a stamp (diameter 6 mm) to press the stamp against the paste inserted into the mould. The testing speed is set to 0.25 mm/s. The maximum force after 4 mm insertion is measured.

Extrusion Force

If desired, the extrusion force can be measured using as testing device a Zwick Z020 machine (Zwick Roell Comp.). The testing device is equipped with a holder for containers and a small stamp to press against the piston inserted in the container and sealing the reservoir. The dimensions of the stamp corresponded to those used in commercially available single container dispensers (commercially available e.g. from 3M Oral Care, 3M ESPE; order code 5706 SD). The feeding speed is set to 1.0 mm/s. The force is measured after the initial yield point was overcome (about 6-9 mm from starting point). The extrusion force is determined as an average value out of six individual measurements.

Gap Resistance

The capability of a paste to open a sulcus and to keep a sulcus open can be determined by a device using a stamp which creates pressure created by a spring onto the curable paste in a small slit (residual gap device).

More precisely, the method can be described as follows:

The gap resistance can be determined as follows:

A mold having a rectangular shape with the dimensions: x (depth)=7.5 mm, y (width)=18.0 mm and z (height)=12.0 mm is provided.

The mold is formed by three immovable and one movable sidewall, all located on a plane surface. The movable sidewall is equipped with a spring having a defined spring pressure of 20N. The spring is compressed and fixed. The moveable sidewall is adjusted to a pre-defined depth 7.5 (cm).

The mold is filled with the curable composition.

After a pre-defined time T1, the fixation of the spring is removed having the result that the spring exerts pressure on the curable composition through the movable sidewall. A portion of the curable composition is pressed out of the mold. The value x (cm) is decreasing.

After a pre-defined time T2, the value x (mm) is determined.

The higher the value x at time T2 is, the higher the consistency of the composition is.

For all results displayed below, T1=60 sec. from filling the gap with the paste and; T2=70 sec. from filling the gap with the paste Water Uptake 0.10 g of the paste was placed in 0.50 g water (app. 20° C.). The paste stayed in contact with water for 2.0 min. Then the paste was removed and the weight of the swollen paste was measured on a scale. The water uptake is calculated as percentage increase of the final weight relation to the original weight (0.1 g).

Figure 2A:
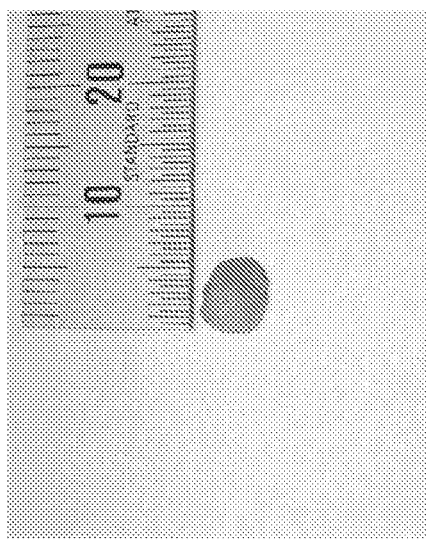
FIG. 2A shows an embodiment of a medical composition not containing carrageenane(s) before contact with water.
Figure 3A:
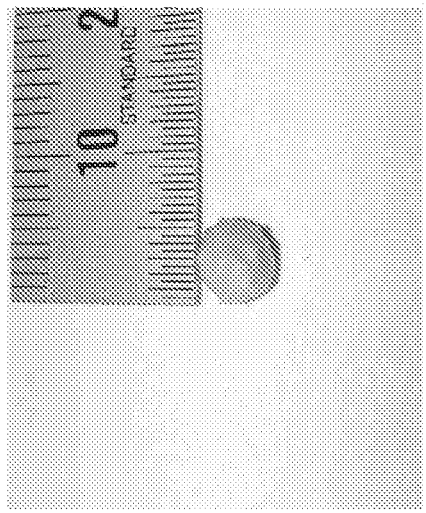
FIG. 3A shows an embodiment of a medical composition not containing carrageenane(s) before contact with water.

Photographs of the pastes of Example 1 and Comparative Examples 2 and 3 before the water uptake test are shown in FIGS. 1a, 2a and 3a.

Figure 1B:
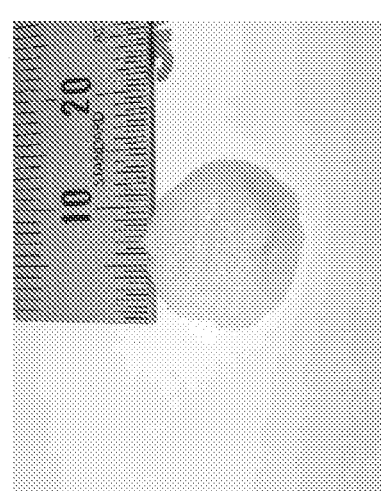
FIG. 1B shows an embodiment of a medical composition described in the present text after contact with water.
Figure 2B:
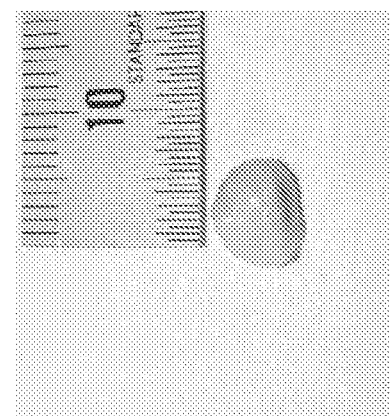
FIG. 2B shows an embodiment of a medical composition not containing carrageenane(s) after contact with water.
Figure 3B:
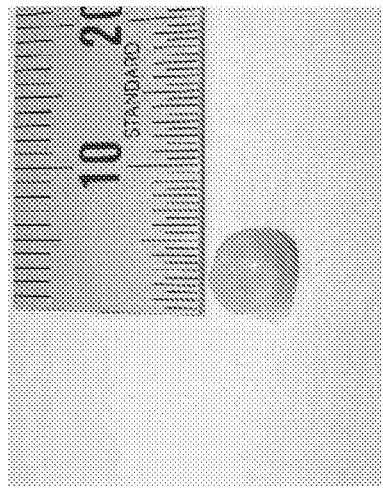
FIG. 3B shows an embodiment of a medical composition not containing carrageenane(s) after contact with water.

Photographs of the pastes of Example 1 and Comparative Examples 2 and 3 after the water uptake test are shown in FIGS. 1b, 2b and 3b.

Materials

TABLE 1

| Component | Description |
| --- | --- |
| Guanidinylated polyethyleneimine | Guanidinyl-containing polymer (g-PEI) |
| Iota-carrageenan | Carrageenan |
| Polyethylene glycol (Mn = 400 g/mol) | Paste forming liquid 1 |
| Pentaerythritol ethoxylate (Mn = 797 g/mol) | Paste forming liquid 2 |
| Mica; particle size: d70 = 1-3 μm | Layer type 1:2 silicate mineral |
| Kaolin; particle size: d50 = about 14 μm | Layer type 1:1 silicate mineral |
| Sikron ™ SF 500 (d95 = 13 μm) | Quartz |
| Pyrogenic Silica-Aerosil ™ 200 (Evonik) | Silica |
| Polydimethylsiloxane, Trimethylsiloxy terminated, CASNR: 63148-62-9 (viscosity 1-10 mPa*s) | Silicone oil |
| Irganox ™ 1010 | Antioxidant |
| Retraction capsules | Capsules in which the commercially available 3M ESPE Astringent Retraction Paste are stored. |

Cross-Linked Guanylated Polyethylenimine (g-PEI)

A 12 L 3-neck split top resin flask was charged with 1250 g of aqueous polyethylenimine solution (mw 75,000, 32.6% solids, BASF Lupasol PS) followed by 1279 g of DI water (de-ionized water). The flask was equipped with an overhead stirrer. 291.6 g of 0-Methylisourea hemisulfate was added and the mixture stirred overnight. An aliquot was taken from the viscous solution and checked by $^1$H NMR (CD$_3$OD) to monitor for the consumption of O-methylisourea hemisulfate. The solution was then transferred to a polypropylene bottle rinsing with a little water followed by measuring percent solids (21.1% by Ohaus).

The solution was then treated with 3401 g of heptanes and the resultant biphasic mixture stirred for 5 minutes. 1,4-Butanediol diglycidyl ether (BUDGE, 91.5 g) was added and the mixture was stirred overnight (16 hours). Stirring was ceased and the heptane and DI water were removed from the mixture with a vacuum filter stick (coarse porosity). The resulting gel was washed with isopropyl alcohol to draw off remaining heptane. 2176 g of isopropyl alcohol was added to the flask. The mixture was stirred vigorously for 10 minutes and then filtered using the filter stick. This procedure was repeated three more times. The resulting white solid was then collected using a Nutsche filter and dried in a vacuum oven at 100° C. to provide the g-PEI in the form of beads.

The dried beads were then jet milled using a 3000 rpm Model 100/20 jet miller. The dried beads were placed in a hopper then feed into an air stream tube. The air stream carried the beads to a splitter where the beads were pushed through two smaller tubes and eventually forced through a cone shaped nozzles (jets). The jets were positioned so the beads collided into each other, the impact reduces the particle size. After the collision, the air stream carried the bead particles to a classifier. The classifier, depending on its rotational speed allowed small particles to be collected while larger particles were returned to the air stream to be jet milled again. Generally, higher classifier speeds result in finer particle size. The jet milled g-PEI beads had an average particle size less than 20 μm.

Preparation of Pastes

TABLE 2

| | Kaolinit | Mica | Quartz | Silica | Silicone oil | Paste forming liquid 1 | Paste forming liquid 2 | g-PEI | Carrageenan | Antioxidant |
| --- | --- | --- | --- | --- | --- | --- | --- | --- | --- | --- |
| Ex. 1 | 3.0 | 22.0 | | | 2.3 | 32.6 | | 20.0 | 20.0 | 0.1 |
| C.E. 2 | 3.0 | 42.0 | | | 2.3 | 32.6 | | | 20.0 | 0.1 |
| C.E. 3 | 3.0 | 40.0 | | | 2.3 | 34.6 | | 20.0 | | 0.1 |
| Ex. 4 | 3.0 | 40.0 | | | 2.3 | 34.6 | | 10.0 | 10.0 | 0.1 |
| Ex. 5 | 2.9 | 20.3 | | | | 29.1 | | 23.8 | 23.8 | 0.1 |
| Ex. 6 | 20.0 | | | | | | 39.9 | 20.0 | 20.0 | 0.1 |
| Ex. 7 | | | 26.9 | 3.0 | | 30.0 | | 20.0 | 20.0 | 0.1 |

The components shown in Table 2 were mixed in a speedmixer under vacuum to obtain a homogenous paste.

The composition of Comparative Example 2 differs from the composition of Example 1 in that instead of g-PEI an equivalent amount of mica was used.

The pastes were filled in retraction capsules and various measurements done. The results are given in Table 3.

TABLE 3

| | Water uptake (weight increase) [%] | Residual gap [mm] |
|---|---|---|
| Ex. 1 | 400 | 5.0 |
| C.E. 2 | 120 | 6.4 |
| C.E. 3 | 0 | 3.9 |
| Ex. 4 | 220 | 4.4 |
| Ex. 5 | 480 | 5.0 |
| Ex. 6 | 420 | 5.4 |
| Ex. 7 | 485 | 5.5 |

The differences in the water-absorption behavior between medical compositions described in the present text comprising the combination of guanidinyl-containing polymer and carrageenan and comparative examples not comprising such a combination can also be demonstrated by showing the water uptake specimens (0.1 g paste), before and after placement in 0.5 ml water. Photographs of the respective samples—before and after water uptake—are shown in FIGS. 1a/b, 2a/b and 3a/b.

The capability to absorb water could be improved if the compositions contained a combination of guanidinyl-containing polymer(s) and carrageenan(s).

In contrast, the compositions containing either guanidinyl-containing polymer or carrageenan alone did not show such an effect.

The residual gap measurement provides evidence that the compositions can be used as dental retraction material, i.e. has the ability to keep the sulcus of a tooth open.

What is claimed is:

1. A medical composition comprising:
   a guanidinyl-containing polymer,
   a carrageenan selected from iota carrageenan and lambda carrageenan, and
   optionally water, if present, in an amount no more than 2 wt % with respect to the weight of the medical composition,
   wherein the medical composition is water absorbing.

2. The medical composition of claim 1, the guanidinyl-containing polymer being:
   a polymer having at least one pendent guanidinyl group characterized by the following formula:

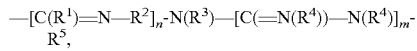

wherein:
   $R^1$ is hydrogen, $C_1$-$C_{12}$ (hetero)alkyl, or a $C_5$-$C_{12}$ (hetero)aryl,
   $R^2$ is a covalent bond, a $C_2$ to $C_{12}$ (hetero)alkylene, or a $C_5$-$C_{12}$ (hetero)arylene,
   $R^3$ is hydrogen, $C_1$-$C_{12}$ (hetero)alkyl, or $C_5$-$C_{12}$ (hetero)aryl,
   each $R^4$ is independently hydrogen, $C_1$-$C_{12}$ (hetero)alkyl, or $C_5$-$C_{12}$ (hetero)aryl,
   $R^5$ is hydrogen, $C_1$-$C_{12}$ (hetero)alkyl, $C_5$-$C_{12}$ (hetero)aryl, or —N($R^4$)$_2$,
   n is 0 or 1, and
   m is 1 or 2.

3. The medical composition of claim 1, the guanidinyl-containing polymer(s) being:
   a polymer having at least one pendent guanidinyl group of the following formula:
   wherein:
   m is equal to 1 or 2,
   $R^3$ is hydrogen, $C_1$-$C_{12}$ (hetero)alkyl, or $C_5$-$C_{12}$ (hetero)aryl,
   each R4 is independently hydrogen, $C_1$-$C_{12}$ (hetero)alkyl, or $C_5$-$C_{12}$ (hetero)aryl, and
   $R^5$ is hydrogen, $C_1$-$C_{12}$ (hetero)alkyl, or $C_5$-$C_{12}$ (hetero)aryl, or —N($R^4$)$_2$; or
   a polymer having at least one pendent guanidinyl group of the following formula:

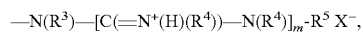

wherein:
   m is equal to 1 or 2,
   $R^3$ is hydrogen, $C_1$-$C_{12}$ (hetero)alkyl, or $C_5$-$C_{12}$ (hetero)aryl,
   each $R^4$ is independently hydrogen, $C_1$-$C_{12}$ (hetero)alkyl, or $C_5$-$C_{12}$ (hetero)aryl,
   $R^5$ is hydrogen, $C_1$-$C_{12}$ (hetero)alkyl, or $C_5$-$C_{12}$ (hetero)aryl, or —N($R^4$)$_2$, and
   $X^-$ is selected from $Cl^-$, $Br^-$, $I^-$, ½ $SO_4^{2-}$, $NO_3^-$, $CH_3COO^-$, $C_3H_7COO^-$.

4. The medical composition of claim 1, the guanidinyl-containing polymer is derived from polyvinylamine, poly(N-methylvinylamine), polyallylamine, polyallylmethylamine, polydiallylamine, poly(-aminomethylstyrene), poly(-aminostyrene), poly(acrylamide-co-methylaminopropylacrylamide), poly(acrylamide-co-aminoethyl-methacrylate), polyethylenimine, polypropylenimine, polylysine, polyaminoamides, polydimethylamine-epichlorohydrin-ethylenediamine, polyaminosiloxanes, dendrimers formed from polyamidoamine and polypropylenimine, biopolymers, polyacrylamide homopolymers, polyacrylamide copolymers, amino-containing polyacrylate homopolymers, or amino-containing polyacrylate copolymers.

5. The medical composition of claim 1, further comprising a filler and a paste forming liquid.

6. The medical composition of claim 5, the filler being selected from silicates, silicas, aluminas, magnesias, titanias, inorganic salts, metallic oxides, glasses, plastic powder, microcrystalline cellulose, nanocrystalline cellulose, starch, and a combination thereof.

7. The medical composition of claim 5, the paste forming liquid being characterized by one or more of the following features:
   molecular weight: 200 to 10,000 g/mol;
   boiling point: above 100° C.; and
   viscosity: up to 35 Pa*s at 23° C.

8. The medical composition of claim 5, being characterized as follows:
   the filler selected from one or more phyllosilicate and being present in an amount from 20 to 70 wt. %;
   the paste forming liquid selected from glycol, glycerine, ethylene glycol, poly(ethylene glycol), propylene glycol, poly(propylene glycol), copolymer(s) of ethylene glycol, propylene glycol, tetrahydrofuran and a combination thereof and being present in an amount from 10 to 60 wt. %;
   the guanidinyl-containing polymer being a polyethylene imine and being present in an amount from 1 to 60 wt. %;

the carrageenane being present in an amount from 1 to 30 wt. %; and the medical composition not comprising one or more of:
aluminum chloride in an amount above 5 wt. %, and water in an amount above 2 wt. %,
wherein wt. % amounts are with respect to the weight of the whole composition.

9. The medical composition of claim 1, comprising the components in following amounts:
a filler(: from 3 to 70 wt. %,
a paste forming liquid: from 10 to 60 wt. %,
the guanidinyl-containing polymer: from 1 to 60 wt. %, and
the carrageenane: from 1 to 40 wt. %,
wherein wt. % amounts are with respect to the weight of the whole composition.

10. The medical composition of claim 1, being contained in a delivery device, the delivery device having the shape of a capsule, compule, syringe, or cartridge.

11. The medical composition of claim 1, for use as a dental retraction material.

12. A kit of parts comprising:
the medical composition of claim 1, and either of the following alone or in combination:
instruction for use;
dental impression material(s);
applier(s);
retraction cap(s).

13. A medical treatment device comprising the medical composition of claim 1.

14. The medical treatment device of claim 13 having the shape of a tape, fixture, wound dressing, bandage, or combination thereof.

15. A method for enhancing the water uptake capability of a medical composition, the method comprising incorporating the medical composition of claim 1 into a medical composition.

16. A method for retracting soft tissue from hard dental tissue, the method comprising:
dispensing a medical composition of claim 1 into a sulcus between the soft tissue and the hard dental tissue;
allowing the medical composition to remain in the sulcus for a period of at least 10 s; and
removing the medical composition from the sulcus.

17. The method of claim 16, further comprising taking an impression of the hard dental tissue with an impression material after the removing of the medical composition from the sulcus.

18. The method of claim 16, further comprising taking an impression of the hard dental tissue via an intra-oral scan using an inter-oral scanner after the removing of the medical composition from the sulcus.

* * * * *

UNITED STATES PATENT AND TRADEMARK OFFICE
CERTIFICATE OF CORRECTION

| | |
|---|---|
| PATENT NO. | : 11,766,386 B2 |
| APPLICATION NO. | : 16/347306 |
| DATED | : September 26, 2023 |
| INVENTOR(S) | : Henning Hoffmann et al. |

It is certified that error appears in the above-identified patent and that said Letters Patent is hereby corrected as shown below:

In the Claims

Column 30
Line 31-32, In Claim 4, delete "poly(-aminomethylstyrene), poly(-aminostyrene)" and insert
-- poly(4-aminomethylstyrene), poly(4-aminostyrene) --, therefor.

Column 31
Line 9, In Claim 9, delete "filler(:" and insert -- filler: --.

Signed and Sealed this
Seventeenth Day of September, 2024

Katherine Kelly Vidal
*Director of the United States Patent and Trademark Office*